United States Patent
Voorhees et al.

(10) Patent No.: US 6,455,070 B1
(45) Date of Patent: Sep. 24, 2002

(54) COMPOSITION FOR TREATING SYMPTOMS OF INFLUENZA

(75) Inventors: John Voorhees, Henderson, NV (US); Leslie Nachman, Henderson, NV (US)

(73) Assignee: East Park Research, Inc., Las Vegas, NV (US)

( * ) Notice: Subject to any disclaimer, the term of this patent is extended or adjusted under 35 U.S.C. 154(b) by 0 days.

(21) Appl. No.: 09/783,027

(22) Filed: Feb. 15, 2001

(51) Int. Cl.[7] .............................. A61K 9/20; A61K 9/48; A61K 9/14
(52) U.S. Cl. ...................... 424/465; 424/464; 424/451; 424/487; 424/761; 424/725
(58) Field of Search .................... 424/489, 464, 424/465, 451, 761, 725

(56) References Cited

U.S. PATENT DOCUMENTS

| | | |
|---|---|---|
| 5,714,150 A | 2/1998 | Nachman |
| 5,834,000 A | 11/1998 | Yng-Wong |
| 5,885,600 A | 3/1999 | Blum et al. |
| 5,989,556 A | 11/1999 | Tsai et al. |
| 6,083,921 A | 7/2000 | Xu |
| 6,126,950 A | 10/2000 | Bindra et al. |
| 6,146,637 A | 11/2000 | Amari |

OTHER PUBLICATIONS

Flu–Ban "Beyond Sympton Relief" Jul. 7, 2000.*
United States Trademark "Flu–Ban", Feb. 23, 1999.*

* cited by examiner

*Primary Examiner*—Thurman K. Page
*Assistant Examiner*—Rachel M. Bennett
(74) *Attorney, Agent, or Firm*—Dennison, Schultz & Dougherty

(57) ABSTRACT

A composition for relief of symptoms of colds and influenza, containing, by weight, about 80–88% olive leaf extract powder containing oleuropein, about 5–10% neem leaf powder and up to about 8% of a homeopathic blend for symptom relief which preferably comprises aconitum napelius, belladonna, eupatorium perfoliatum, gelsemium sempervirens, *Echinacea angustifolia* and ferrum phosphoricum.

7 Claims, No Drawings

COMPOSITION FOR TREATING SYMPTOMS OF INFLUENZA

BACKGROUND OF THE INVENTION

The invention relates to the field of natural compositions, particularly herbal compositions, for treating symptoms of influenza.

Colds and influenza are major causes of illness and loss of productivity both within the United States, and throughout the world at large. Approximately 10–15% of adult colds are thought to be caused by viruses which are also responsible for other serious illnesses, including influenza.

An effective treatment for a wide variety of illnesses caused by viruses and bacteria has long been sought, both in terms of antiviral and antimicrobial action, and in terms of symptom relief. Some traditional Chinese medicine herbal formulas have been found somewhat effective in this regard, as is disclosed, for example, in U.S. Pat. Nos. 5,834,000, 5,989,556 and 6,083,291. Some of the traditional compositions have contained stimulants such as caffeine and ephedrine, which have proved to be undesirable.

One material which has been found to have antiviral properties is oleuropein. Oleuropein is a bitter glucoside found in olives and the roots, leaves and bark of the olive tree, Olea europaea. Medicinal use of this extract dates back to the early 1800s when it was used in liquid form as a treatment for malarial infections. Oleuropein undergoes mild acid hydrolysis to form elenolic acid, this process being similar to an enzyme based hydrolysis of the compound which takes place in the human body. A salt of elenolic acid, calcium elenolate, was reported to have in vitro antiviral activity in an article by Renis, "In Vitro Antiviral Activity of Calcium Elenolate," Antimicrobial Agents and Chemotherapy—1969, pages 167–172. In this article, calcium elenolate was reported to have activity against a wide variety of viruses, with the greatest activity under alkaline conditions (pH 7.5).

However, when incubation was carried out with amino acids prior to incubation with virus, losses in virucidal activity were detected, especially in the presence of glycine, lysine, cysteine and histidine, and to a lesser extent with other amino acids. More recently, oleuropein has been found to be effective, in-vitro, against Salmonella enteritidis ("Inhibition of Salmonella enteritidis by oleuropein in broth and in a model food system," Lett Appl Microbiol 20(2):120–4, Febuary, 1995), and enterotoxin B ("The effect of the olive phenolic compound, oleuropein, on growth and enterotoxin B U) production," J. Appl. Bacteriology 74(3):253–9, March, 1993). In addition, oleuropein has been found to protect low density lipoprotein from oxidation (Life Sci 55(24):1965–71, 1994) and to inhibit platelet aggregation (Thromb Res 78(2):151–60, Apr. 15, 1995). U.S. Pat. No. 5,714,150 discloses a method for extracting oleuropein from olive leaves in a form which retains medicinal activity in vivo, with multiple extractions taking place with a hydroethanolic solvent, followed by distillation under vacuum to produce and concentrate, and then drying. The steps take place at about 20 to 88° C.

SUMMARY OF THE INVENTION

It is therefore an object of the invention to provide a pharmacologically effective composition which is effective against a broad spectrum of viruses and bacteria.

It is another object of the invention to provide a composition which is completely plant based in nature and does not contain caffeine, ephedrine, or similar undesirable components.

It is a further object of the invention to provide a composition which alleviates symptoms of colds and influenza.

To achieve these and other objects, the invention is directed to a composition for relief of symptoms of colds and influenza, comprising, by weight, about 80–88% olive leaf extract powder containing oleuropein, about 5–10% neem leaf powder and about 4–8% of a homeopathic blend for symptom relief, and which preferably comprises one or more components from the group aconitum napelius, belladonna, eupatorium perfoliatum, gelsemium sermpervirens, Echinacea angustifolia and ferrum phosphoricum.

The invention also relates to a method of substantially eliminating or ameliorating the symptoms of viral and microbial illness of human patients comprising administering to a human patient in need of thereof an effective amount of a composition such as set forth above.

DETAILED DESCRIPTION OF THE INVENTION

The major ingredient of the composition of the invention is an olive leaf extract powder, the olive leaf preferably extracted according to the disclosure of U.S. Pat. No. 5,714,150, which is incorporated herein by reference. In that process, olive leaves are treated with an alcohol and water solution to produce an alcoholic extract, the alcohol and water solution is drained from the olive leaves, the olive leaves are treated with fresh alcohol and water solution at least two more times, the hydroethanolic extracts produced are then combined and distilled under vacuum at a temperature of about 20° to 88° C. to produce a concentrated extract having a solids content of about 30 to 40%. The concentrated extract can then be spray dried or oven dried under vacuum to produce a dry powder extract comprising approximately 30–40% by weight oleuropein.

Importantly, these process steps must be conducted at a temperature no greater than about 88° C., since destruction of the effective glucoside is thought to occur at higher temperatures. It is thought that by conducting a plurality of low temperature hydroethanolic extractions followed by a low temperature distillation, the resultant oleuropein contains a high proportion of R-oleuropein as compared with L-oleuropein, the d-oleuropein not binding to amino acids or serum proteins in the human body, and therefore remaining active in vivo.

In keeping with the low temperature processing requirements, the olive leaf concentrate can also be dried by freeze drying. Applicants believe that a more potent extract can be obtained by freeze drying. The composition of the invention will contain about 80–88% by weight olive leaf extract powder, preferably about 84–86% by weight.

The composition of the invention will also contain about 5–10% by weight neem leaf extract. The neem tree, also known as Azadiracha indica, has for many centuries been a source of herbal medicines on the Indian subcontinent. A number of uses for neem extracts are known, including the use of neem oil as an insect repellant (U.S. Pat. No. 5,885,600) and the use of neem extract for healing the skin (U.S. Pat. No. 6,126,950).

The composition of the invention contains about 5–10% by weight of a hydroethanolic extract of neem leaf, dried to a powder form. This material is available commercially from, for example, Rym Exports of Worli, Mumbai, India.

Preferably, the composition of the invention also contains up to about 8% by weight of a homeopathic blend useful in reducing symptoms of colds and fevers. A preferred blend contains aconitum napelius, belladonna, eupatorium perfoliatum, gelsemium sempervirens, Echinacea angostifolia and ferrum phosphoricum. Aconitum napelius, belladonna and ferrum phosphoricum are used for treatment of fever, eupatorium perfoliatum and gelsemium sempervirens are used to relieve symptoms of aches and pains, headaches and trembling, and Echinacea angustifolia is used for treatment of infections. This blend is typically added in an amount of about 6–8% by weight. Other blends including some of the above materials, or other material for the same general purposes may also be used in effective amounts.

In addition to the above ingredients, the compositions of the invention will typically contain pharmaceutically acceptable excipients of the type well known in the art necessary for proper tableting of the composition. Such excipients may make up about 10–20% by weight of the final tablet.

A typical tablet or capsule according to the invention will contain about 500 mg olive leaf extract powder, 50 mg neem leaf extract powder and 40 mg of the homeopathic blend, all weights ±10%. The adult dosage of this composition is 2 tablets or capsules, 4 times a day, at the first sign of a cold or flu, taken with a large quantity of water. While symptoms may disappear rapidly, the treatment should be continued for at least three days for best effect.

While not wishing to be held to any particular theory, Applicants recognize that various olive extracts have been known to be effective against viruses for many years, and the neem leaf which has been long used in Asia for symptom relief, is thought to provide additional bacteriacidal and virucidal properties.

What is claimed is:

1. A composition for relief of symptoms of colds and influenza, consisting essentially of, by weight, about 80–88% freeze dried olive leaf extract powder containing oleuropein, about 5–10% neem leaf powder and up to about 8% of a homeopathic blend for symptom relief.

2. The composition of claim 1, wherein the olive leaf extract is present in an amount of about 84–86% by weight.

3. The composition of claim 1, formulated into dosage units containing 450–550 mg olive leaf extract, 45–55 mg neem leaf extract and 36–44 mg of said homeopathic blend.

4. The composition of claim 1, containing about 6 to 8% by weight of a homeopathic blend containing at least one component selected from the group consisting of aconitum napelius, belladonna, eupatorium perfoliatum, gelsemium sempervirens, *Echinacea angustifolia* and ferrum phosphoricum.

5. The composition of claim 4 containing about 6 to 8% by weight of a homeopathic blend containing aconitum napelius, belladonna, eupatorium perfoliatum, gelsemium sempervirens, *Echinacea angustifolia* and ferrum phosphoricum.

6. A method of ameliorating symptoms of colds and flu in human patients comprising administering to a patient in need thereof a composition consisting essentially of, by weight, about 80–88% freeze dried olive leaf extract powder containing oleuropein, about 5–10% neem leaf powder and about 4–8% of a homeopathic blend for symptom relief.

7. The method of claim 6, wherein the homeopathic blend comprises at least one component selected from the group consisting of aconitum napelius, belladonna, eupatorium perfoliatum, gelsemium sempervirens, *Echinacea angustifolia* and ferrum phosphoricum.

* * * * *